United States Patent [19]

Xu et al.

[11] Patent Number: 5,532,153
[45] Date of Patent: Jul. 2, 1996

[54] METHOD FOR CLONING AND PRODUCING THE SACI RESTRICTION ENDONUCLEASE

[75] Inventors: Shuang-yong Xu, Lexington; Jianping Xiao, Wenham, both of Mass.

[73] Assignee: New England Biolabs, Inc., Beverly, Mass.

[21] Appl. No.: 409,199

[22] Filed: Mar. 23, 1995

[51] Int. Cl.$^6$ .............................. C12N 9/22; C12N 15/55
[52] U.S. Cl. .................. 435/199; 435/193; 435/320.1; 435/252.33; 536/23.2
[58] Field of Search ..................... 435/199, 193, 435/320.1, 252.33; 536/23.2

[56] References Cited

FOREIGN PATENT DOCUMENTS 0193413  9/1986  European Pat. Off. .

OTHER PUBLICATIONS

Kosykh, et al., Molec. Gen. Genet. 178:717–719 (1980).
Mann, et al., Gene, 3:97–112 (1978).
Walder, Proc. Natl. Acad. Sci. USA, 78:1503–1507 (1981).
Bougueleret, Nucl. Acids Res. 12:3659–3676 (1984).
Gingeras and Brooks, Proc. Natl. Acad. Sci. USA 80:402–406 (1983).
Theriault and Roy, Gene, 19:355–359 (1982).
Blumenthal, J. Bacteriol. 164:501–509 (1985).
Kiss, Nucl. Acids Res., 13:6403–6421 (1985).
Szomolanyi, Gene, 10:219–225 (1980).
Janulaitis, Gene, 20:197–204 (1982).
Kiss and Baldauf, Gene, 21:111–119 (1983).
Walder, J. Bio. Chem., 258:1235–1241 (1983).
Fomenkov, et al., Nucl. Acids Res., 22:2399–2403 (1994).
Raleigh and Wilson, Proc. Natl. Acad. Sci. USA, 83:9070–9074 (1986).
Skoglund, Gene, 88:1–5 (1990).
Stoker, et al., Gene, 18:335–341 (1982).
Ochman, et al., Bio/Technology, 8:759–760 (1990).

*Primary Examiner*—Charles L. Patterson, Jr.
*Attorney, Agent, or Firm*—Gregory D. Williams

[57] ABSTRACT

The present invention relates to recombinant DNA which encodes the SacI restriction endonuclease and modification methylase, and production of SacI restriction endonuclease from the recombinant DNA.

6 Claims, 3 Drawing Sheets

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 12 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:1:

GGAGGTAAAT AA           12

( 2 ) INFORMATION FOR SEQ ID NO:2:

( i ) SEQUENCE CHARACTERISTICS:
( A ) LENGTH: 1168 base pairs
( B ) TYPE: nucleic acid
( C ) STRANDEDNESS: unknown
( D ) TOPOLOGY: unknown ( i i ) MOLECULE TYPE: DNA (genomic)

( i x ) FEATURE:
( A ) NAME/KEY: CDS
( B ) LOCATION: 1..1167

( x i ) SEQUENCE DESCRIPTION: SEQ ID NO:2:

| GTG | AAC | CAT | GAG | CTT | CCT | GTG | ATC | AGT | CTG | TTC | TCC | GGG | GCC | GGT | GGC | 48 |
|---|---|---|---|---|---|---|---|---|---|---|---|---|---|---|---|---|
| Met | Asn | His | Glu | Leu | Pro | Val | Ile | Ser | Leu | Phe | Ser | Gly | Ala | Gly | Gly | |
| 1 | | | | 5 | | | | | 10 | | | | | 15 | | |

| CTC | GAC | TGC | GCC | ATC | GAG | AGC | TGC | GCT | GAG | CCA | CCG | CTG | GTC | CAG | GAC | 96 |
|---|---|---|---|---|---|---|---|---|---|---|---|---|---|---|---|---|
| Leu | Asp | Cys | Ala | Ile | Glu | Ser | Cys | Ala | Glu | Pro | Pro | Leu | Val | Gln | Asp | |
| | | | 20 | | | | | 25 | | | | | 30 | | | |

| GGC | TCC | GGG | TCT | CCG | CTA | CGT | GTC | GCG | GTT | GCC | ACT | GAC | TAT | GAG | CAG | 144 |
|---|---|---|---|---|---|---|---|---|---|---|---|---|---|---|---|---|
| Gly | Ser | Gly | Ser | Pro | Leu | Arg | Val | Ala | Val | Ala | Thr | Asp | Tyr | Glu | Gln | |
| | | 35 | | | | | 40 | | | | | 45 | | | | |

| ACC | GCT | CTG | GAT | ACA | CTG | TCG | GCC | AAC | TTC | CCG | CAC | ACC | AAG | ACG | CTG | 192 |
|---|---|---|---|---|---|---|---|---|---|---|---|---|---|---|---|---|
| Thr | Ala | Leu | Asp | Thr | Leu | Ser | Ala | Asn | Phe | Pro | His | Thr | Lys | Thr | Leu | |
| | 50 | | | | | 55 | | | | | 60 | | | | | |

| TGT | GGG | GAT | ATC | CAA | ACG | ATC | CCG | ACC | GCA | GAG | TTG | CTG | GAA | GCC | GGC | 240 |
|---|---|---|---|---|---|---|---|---|---|---|---|---|---|---|---|---|
| Cys | Gly | Asp | Ile | Gln | Thr | Ile | Pro | Thr | Ala | Glu | Leu | Leu | Glu | Ala | Gly | |
| 65 | | | | | 70 | | | | | 75 | | | | | 80 | |

| GGG | CTG | AAG | CCC | GGC | GAT | CCC | ACC | CTG | GTC | ATC | GGT | GGT | CCT | CCT | TGT | 288 |
|---|---|---|---|---|---|---|---|---|---|---|---|---|---|---|---|---|
| Gly | Leu | Lys | Pro | Gly | Asp | Pro | Thr | Leu | Val | Ile | Gly | Gly | Pro | Pro | Cys | |
| | | | | 85 | | | | | 90 | | | | | 95 | | |

| ACG | CCG | TTC | AGT | AAG | TCC | GGA | TTC | TGG | ATC | GAG | GAG | AAG | CGC | AAC | AGC | 336 |
|---|---|---|---|---|---|---|---|---|---|---|---|---|---|---|---|---|
| Thr | Pro | Phe | Ser | Lys | Ser | Gly | Phe | Trp | Ile | Glu | Glu | Lys | Arg | Asn | Ser | |
| | | | 100 | | | | | 105 | | | | | 110 | | | |

| GCC | GAT | CCC | AAT | GCC | TCC | CTC | CTT | GAC | GAG | TAC | GTC | CGT | GTG | GTT | CGG | 384 |
|---|---|---|---|---|---|---|---|---|---|---|---|---|---|---|---|---|
| Ala | Asp | Pro | Asn | Ala | Ser | Leu | Leu | Asp | Glu | Tyr | Val | Arg | Val | Val | Arg | |
| | | 115 | | | | | 120 | | | | | 125 | | | | |

| GAG | AGC | AAG | CCC | GAA | GCC | TTC | ATC | CTG | GAA | AAT | GTG | CAG | GGC | CTG | ACG | 432 |
|---|---|---|---|---|---|---|---|---|---|---|---|---|---|---|---|---|
| Glu | Ser | Lys | Pro | Glu | Ala | Phe | Ile | Leu | Glu | Asn | Val | Gln | Gly | Leu | Thr | |
| | 130 | | | | | 135 | | | | | 140 | | | | | |

| TAC | AAG | ACC | CAT | CAG | GCT | CAG | TTC | GAC | CGA | CTC | ATT | GCG | GGC | CTT | AAG | 480 |
|---|---|---|---|---|---|---|---|---|---|---|---|---|---|---|---|---|
| Tyr | Lys | Thr | His | Gln | Ala | Gln | Phe | Asp | Arg | Leu | Ile | Ala | Gly | Leu | Lys | |
| 145 | | | | | 150 | | | | | 155 | | | | | 160 | |

| GAT | GCG | GGC | TAC | AAC | CCG | ACG | TTC | CGT | GTG | CTC | CTT | GCG | GCC | GAG | TAT | 528 |

```
                Asp  Ala  Gly  Tyr  Asn  Pro  Thr  Phe  Arg  Val  Leu  Leu  Ala  Ala  Glu  Tyr
                                    165                     170                         175

GGG  GTT  CCG  CAG  CTC  CGC  AGG  CGA  GTA  TTC  GTT  GTG  GGG  CGA  CGT  GAC            576
Gly  Val  Pro  Gln  Leu  Arg  Arg  Arg  Val  Phe  Val  Val  Gly  Arg  Arg  Asp
               180                     185                     190

GGT  AAG  GCT  TTC  CAC  TTC  CCC  GAA  ACC  ACG  CAC  TCT  GGC  GAG  TCG  GAG            624
Gly  Lys  Ala  Phe  His  Phe  Pro  Glu  Thr  Thr  His  Ser  Gly  Glu  Ser  Glu
          195                     200                          205

CGG  GAT  CGG  GTG  ATT  GAT  CAC  ACC  AAG  ATT  CCG  TTC  ACG  AGT  CTT  CGC            672
Arg  Asp  Arg  Val  Ile  Asp  His  Thr  Lys  Ile  Pro  Phe  Thr  Ser  Leu  Arg
     210                     215                          220

GAG  GCA  CTT  GCC  GGA  CTG  CCG  GAC  GTT  CCT  GAG  GCT  GGA  GAA  GTT  GTT            720
Glu  Ala  Leu  Ala  Gly  Leu  Pro  Asp  Val  Pro  Glu  Ala  Gly  Glu  Val  Val
225                      230                     235                         240

GAG  GGA  ACC  TAC  GCC  GAA  CTC  GCT  GCG  GAA  GTT  CCT  CCT  GGG  CAA  AAC            768
Glu  Gly  Thr  Tyr  Ala  Glu  Leu  Ala  Ala  Glu  Val  Pro  Pro  Gly  Gln  Asn
                    245                          250                         255

TAC  CTA  TGG  CAC  ACC  GAC  CGA  TAT  GGC  GGT  CGC  AAC  GAG  TTC  AAA  TGG            816
Tyr  Leu  Trp  His  Thr  Asp  Arg  Tyr  Gly  Gly  Arg  Asn  Glu  Phe  Lys  Trp
               260                          265                     270

CGT  AGC  CGC  TAT  TGG  ACC  TTC  CTG  CTG  AAG  GCG  GAC  CCA  GAC  CGC  CCT            864
Arg  Ser  Arg  Tyr  Trp  Thr  Phe  Leu  Leu  Lys  Ala  Asp  Pro  Asp  Arg  Pro
          275                     280                          285

TCT  ACG  ACG  CTG  CAG  GCT  CAG  CCA  GGT  CCA  TGG  GTC  GGA  CCA  TTT  CAC            912
Ser  Thr  Thr  Leu  Gln  Ala  Gln  Pro  Gly  Pro  Trp  Val  Gly  Pro  Phe  His
     290                     295                          300

TGG  GAG  AAC  GTG  AAG  AAC  GCG  AAC  GGG  GAA  GAG  CGA  GCG  CGT  AGG  TTT            960
Trp  Glu  Asn  Val  Lys  Asn  Ala  Asn  Gly  Glu  Glu  Arg  Ala  Arg  Arg  Phe
305                      310                     315                         320

CGC  GTT  GCC  GAA  ATG  AAG  CGG  ATC  ATG  ACT  TTC  CCT  GAT  GAG  TTC  GTT           1008
Arg  Val  Ala  Glu  Met  Lys  Arg  Ile  Met  Thr  Phe  Pro  Asp  Glu  Phe  Val
                    325                          330                        335

TTC  ACC  GGA  GTG  AAG  CGC  GAG  GTG  CAG  CGG  CAG  ATC  GGT  AAT  CCC  GTC           1056
Phe  Thr  Gly  Val  Lys  Arg  Glu  Val  Gln  Arg  Gln  Ile  Gly  Asn  Pro  Val
               340                     345                          350

CCG  GTG  GAG  TTG  GGG  AAG  GTC  GTC  GTC  CGG  GCC  CTG  ATG  GAA  CAA  CTC           1104
Pro  Val  Glu  Leu  Gly  Lys  Val  Val  Val  Arg  Ala  Leu  Met  Glu  Gln  Leu
          355                     360                          365

GGC  TAT  CTT  GAT  TCT  CGC  GGT  ACT  ACT  ATT  CCT  AGC  CAG  GCT  GGA  CAC           1152
Gly  Tyr  Leu  Asp  Ser  Arg  Gly  Thr  Thr  Ile  Pro  Ser  Gln  Ala  Gly  His
     370                     375                          380

GAA  CAG  CTT  GAA  TTG  A                                                               1168
Glu  Gln  Leu  Glu  Leu
385
```

( 2 ) INFORMATION FOR SEQ ID NO:3:

( i ) SEQUENCE CHARACTERISTICS:
        ( A ) LENGTH: 389 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met  Asn  His  Glu  Leu  Pro  Val  Ile  Ser  Leu  Phe  Ser  Gly  Ala  Gly  Gly
1                   5                    10                         15

Leu  Asp  Cys  Ala  Ile  Glu  Ser  Cys  Ala  Glu  Pro  Pro  Leu  Val  Gln  Asp
               20                    25                     30

Gly  Ser  Gly  Ser  Pro  Leu  Arg  Val  Ala  Val  Ala  Thr  Asp  Tyr  Glu  Gln
          35                      40                          45
```

| | | | | | | | | | | | | | | |
|---|---|---|---|---|---|---|---|---|---|---|---|---|---|---|
| Thr | Ala | Leu | Asp | Thr | Leu | Ser | Ala | Asn | Phe | Pro | His | Thr | Lys | Thr | Leu |
| | 50 | | | | | 55 | | | | | 60 | | | | |
| Cys | Gly | Asp | Ile | Gln | Thr | Ile | Pro | Thr | Ala | Glu | Leu | Leu | Glu | Ala | Gly |
| 65 | | | | | 70 | | | | 75 | | | | | | 80 |
| Gly | Leu | Lys | Pro | Gly | Asp | Pro | Thr | Leu | Val | Ile | Gly | Gly | Pro | Pro | Cys |
| | | | | 85 | | | | | 90 | | | | | 95 | |
| Thr | Pro | Phe | Ser | Lys | Ser | Gly | Phe | Trp | Ile | Glu | Glu | Lys | Arg | Asn | Ser |
| | | | 100 | | | | | 105 | | | | | 110 | | |
| Ala | Asp | Pro | Asn | Ala | Ser | Leu | Leu | Asp | Glu | Tyr | Val | Arg | Val | Val | Arg |
| | | 115 | | | | | 120 | | | | | 125 | | | |
| Glu | Ser | Lys | Pro | Glu | Ala | Phe | Ile | Leu | Glu | Asn | Val | Gln | Gly | Leu | Thr |
| | 130 | | | | | 135 | | | | | 140 | | | | |
| Tyr | Lys | Thr | His | Gln | Ala | Gln | Phe | Asp | Arg | Leu | Ile | Ala | Gly | Leu | Lys |
| 145 | | | | | 150 | | | | | 155 | | | | | 160 |
| Asp | Ala | Gly | Tyr | Asn | Pro | Thr | Phe | Arg | Val | Leu | Leu | Ala | Ala | Glu | Tyr |
| | | | | 165 | | | | | 170 | | | | | 175 | |
| Gly | Val | Pro | Gln | Leu | Arg | Arg | Arg | Val | Phe | Val | Val | Gly | Arg | Arg | Asp |
| | | | 180 | | | | | 185 | | | | | 190 | | |
| Gly | Lys | Ala | Phe | His | Phe | Pro | Glu | Thr | Thr | His | Ser | Gly | Glu | Ser | Glu |
| | | 195 | | | | | 200 | | | | | 205 | | | |
| Arg | Asp | Arg | Val | Ile | Asp | His | Thr | Lys | Ile | Pro | Phe | Thr | Ser | Leu | Arg |
| | 210 | | | | | 215 | | | | | 220 | | | | |
| Glu | Ala | Leu | Ala | Gly | Leu | Pro | Asp | Val | Pro | Glu | Ala | Gly | Glu | Val | Val |
| 225 | | | | | 230 | | | | | 235 | | | | | 240 |
| Glu | Gly | Thr | Tyr | Ala | Glu | Leu | Ala | Ala | Glu | Val | Pro | Pro | Gly | Gln | Asn |
| | | | | 245 | | | | | 250 | | | | | 255 | |
| Tyr | Leu | Trp | His | Thr | Asp | Arg | Tyr | Gly | Gly | Arg | Asn | Glu | Phe | Lys | Trp |
| | | | 260 | | | | | 265 | | | | | 270 | | |
| Arg | Ser | Arg | Tyr | Trp | Thr | Phe | Leu | Leu | Lys | Ala | Asp | Pro | Asp | Arg | Pro |
| | | 275 | | | | | 280 | | | | | 285 | | | |
| Ser | Thr | Thr | Leu | Gln | Ala | Gln | Pro | Gly | Pro | Trp | Val | Gly | Pro | Phe | His |
| | 290 | | | | | 295 | | | | | 300 | | | | |
| Trp | Glu | Asn | Val | Lys | Asn | Ala | Asn | Gly | Glu | Glu | Arg | Ala | Arg | Arg | Phe |
| 305 | | | | | 310 | | | | | 315 | | | | | 320 |
| Arg | Val | Ala | Glu | Met | Lys | Arg | Ile | Met | Thr | Phe | Pro | Asp | Glu | Phe | Val |
| | | | | 325 | | | | | 330 | | | | | 335 | |
| Phe | Thr | Gly | Val | Lys | Arg | Glu | Val | Gln | Arg | Gln | Ile | Gly | Asn | Pro | Val |
| | | | 340 | | | | | 345 | | | | | 350 | | |
| Pro | Val | Glu | Leu | Gly | Lys | Val | Val | Val | Arg | Ala | Leu | Met | Glu | Gln | Leu |
| | | 355 | | | | | 360 | | | | | 365 | | | |
| Gly | Tyr | Leu | Asp | Ser | Arg | Gly | Thr | Thr | Ile | Pro | Ser | Gln | Ala | Gly | His |
| | 370 | | | | | 375 | | | | | 380 | | | | |
| Glu | Gln | Leu | Glu | Leu | | | | | | | | | | | |
| 385 | | | | | | | | | | | | | | | |

( 2 ) INFORMATION FOR SEQ ID NO:4:

( i ) SEQUENCE CHARACTERISTICS:
        ( A ) LENGTH: 1077 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..1074

( x i ) SEQUENCE DESCRIPTION: SEQ ID NO:4:

| | | | | | | | | | | | | | | | | |
|---|---|---|---|---|---|---|---|---|---|---|---|---|---|---|---|---|
| ATG | GGA | ATA | ACA | ATT | AAA | AAG | AGC | ACG | GCG | GAG | CAG | GTT | TTG | AGG | AAG | 48 |
| Met | Gly | Ile | Thr | Ile | Lys | Lys | Ser | Thr | Ala | Glu | Gln | Val | Leu | Arg | Lys | |
| 1 | | | | 5 | | | | | 10 | | | | | 15 | | |
| GCG | TAC | GAG | GCG | GCC | GCT | TCG | GAT | GAT | GTA | TTC | CTC | GAA | GAT | TGG | ATA | 96 |
| Ala | Tyr | Glu | Ala | Ala | Ala | Ser | Asp | Asp | Val | Phe | Leu | Glu | Asp | Trp | Ile | |
| | | | 20 | | | | | 25 | | | | | 30 | | | |
| TTT | CTG | GCT | ACT | TCG | CTA | CGC | GAG | GTA | GAT | GCT | CCA | AGG | ACT | TAC | ACG | 144 |
| Phe | Leu | Ala | Thr | Ser | Leu | Arg | Glu | Val | Asp | Ala | Pro | Arg | Thr | Tyr | Thr | |
| | | 35 | | | | | 40 | | | | | 45 | | | | |
| GCT | GCG | CTT | GTG | ACA | GCA | CTG | CTC | GCG | CGT | GCA | TGT | GAC | GAC | AGG | GTT | 192 |
| Ala | Ala | Leu | Val | Thr | Ala | Leu | Leu | Ala | Arg | Ala | Cys | Asp | Asp | Arg | Val | |
| | 50 | | | | | 55 | | | | | 60 | | | | | |
| GAC | CCA | CGC | TCT | ATC | AAA | GAG | AAG | TAC | GAC | GAT | CGC | GCC | TTC | TCT | CTG | 240 |
| Asp | Pro | Arg | Ser | Ile | Lys | Glu | Lys | Tyr | Asp | Asp | Arg | Ala | Phe | Ser | Leu | |
| 65 | | | | | 70 | | | | | 75 | | | | | 80 | |
| CGT | ACC | CTT | TGC | CAC | GGT | GTA | GTG | GTT | CCG | ATG | TCC | GTA | GAA | CTT | GGA | 288 |
| Arg | Thr | Leu | Cys | His | Gly | Val | Val | Val | Pro | Met | Ser | Val | Glu | Leu | Gly | |
| | | | | 85 | | | | | 90 | | | | | 95 | | |
| TTT | GAT | CTG | GGG | GCT | ACG | GGC | CGC | GAG | CCG | ATC | AAC | AAT | CAG | CCA | TTC | 336 |
| Phe | Asp | Leu | Gly | Ala | Thr | Gly | Arg | Glu | Pro | Ile | Asn | Asn | Gln | Pro | Phe | |
| | | | 100 | | | | | 105 | | | | | 110 | | | |
| TTC | CGT | TAC | GAC | CAA | TAC | AGC | GAG | ATC | GTC | AGG | GTC | CAG | ACG | AAG | GCG | 384 |
| Phe | Arg | Tyr | Asp | Gln | Tyr | Ser | Glu | Ile | Val | Arg | Val | Gln | Thr | Lys | Ala | |
| | | 115 | | | | | 120 | | | | | 125 | | | | |
| CGC | CCC | TAT | CTG | GAC | CGA | GTA | AGC | AGT | GCC | CTT | GCT | AGG | GTC | GAT | GAA | 432 |
| Arg | Pro | Tyr | Leu | Asp | Arg | Val | Ser | Ser | Ala | Leu | Ala | Arg | Val | Asp | Glu | |
| | 130 | | | | | 135 | | | | | 140 | | | | | |
| GAA | GAC | TAT | TCC | ACT | GAA | GAG | TCG | TTC | CGA | GCG | CTT | GTC | GCT | GTC | TTG | 480 |
| Glu | Asp | Tyr | Ser | Thr | Glu | Glu | Ser | Phe | Arg | Ala | Leu | Val | Ala | Val | Leu | |
| 145 | | | | | 150 | | | | | 155 | | | | | 160 | |
| GCC | GTG | TGT | ATC | TCT | GTG | GCG | AAC | AAA | AAG | CAG | CGC | GTT | GCC | GTC | GGG | 528 |
| Ala | Val | Cys | Ile | Ser | Val | Ala | Asn | Lys | Lys | Gln | Arg | Val | Ala | Val | Gly | |
| | | | | 165 | | | | | 170 | | | | | 175 | | |
| AGT | GCC | ATC | GTC | GAG | GCG | AGC | CTA | ATC | GCT | GAG | ACT | CAG | AGC | TTC | GTT | 576 |
| Ser | Ala | Ile | Val | Glu | Ala | Ser | Leu | Ile | Ala | Glu | Thr | Gln | Ser | Phe | Val | |
| | | | 180 | | | | | 185 | | | | | 190 | | | |
| GTG | AGT | GGC | CAC | GAC | GTT | CCA | CGA | AAG | CTG | CAG | GCT | TGT | GTT | GCG | GCT | 624 |
| Val | Ser | Gly | His | Asp | Val | Pro | Arg | Lys | Leu | Gln | Ala | Cys | Val | Ala | Ala | |
| | | 195 | | | | | 200 | | | | | 205 | | | | |
| GGT | CTT | GAC | ATG | GTC | TAC | AGC | GAG | GTC | GTC | TCG | CGG | AGG | ATC | AAT | GAC | 672 |
| Gly | Leu | Asp | Met | Val | Tyr | Ser | Glu | Val | Val | Ser | Arg | Arg | Ile | Asn | Asp | |
| | | 210 | | | | | 215 | | | | | 220 | | | | |
| CCT | TCT | CGC | GAC | TTT | CCT | GGT | GAC | GTC | CAA | GTG | ATT | TTG | GAC | GGC | GAT | 720 |
| Pro | Ser | Arg | Asp | Phe | Pro | Gly | Asp | Val | Gln | Val | Ile | Leu | Asp | Gly | Asp | |
| 225 | | | | | 230 | | | | | 235 | | | | | 240 | |
| CCA | TTG | CTT | ACC | GTT | GAA | GTG | CGT | GGA | AAG | AGC | GTG | TCG | TGG | GAG | GGG | 768 |
| Pro | Leu | Leu | Thr | Val | Glu | Val | Arg | Gly | Lys | Ser | Val | Ser | Trp | Glu | Gly | |
| | | | | 245 | | | | | 250 | | | | | 255 | | |
| CTT | GAG | CAA | TTC | GTC | AGC | AGT | GCA | ACG | TAT | GCC | GGC | TTC | CGA | CGA | GTT | 816 |
| Leu | Glu | Gln | Phe | Val | Ser | Ser | Ala | Thr | Tyr | Ala | Gly | Phe | Arg | Arg | Val | |
| | | | 260 | | | | | 265 | | | | | 270 | | | |
| GCG | CTC | ATG | GTC | GAT | GCG | GCG | TCG | CAC | GTG | TCG | CTT | ATG | TCG | GCC | GAT | 864 |
| Ala | Leu | Met | Val | Asp | Ala | Ala | Ser | His | Val | Ser | Leu | Met | Ser | Ala | Asp | |
| | | 275 | | | | | 280 | | | | | 285 | | | | |
| GAT | CTG | ACC | AGC | GCG | CTT | GAG | CGG | AAG | TAC | GAG | TGC | ATC | GTC | AAG | GTG | 912 |
| Asp | Leu | Thr | Ser | Ala | Leu | Glu | Arg | Lys | Tyr | Glu | Cys | Ile | Val | Lys | Val | |
| | 290 | | | | | 295 | | | | | 300 | | | | | |
| AAC | GAG | AGC | GTG | TCG | AGC | TTC | CTG | CGT | GAC | GTA | TTC | GTC | TGG | TCG | CCT | 960 |

```
Asn  Glu  Ser  Val  Ser  Ser  Phe  Leu  Arg  Asp  Val  Phe  Val  Trp  Ser  Pro
305                      310                     315                     320

CGC  GAC  GTC  CAC  TCG  ATT  CTT  TCG  GCC  TTT  CCT  GAG  GCA  ATG  TAT  CGC    1008
Arg  Asp  Val  His  Ser  Ile  Leu  Ser  Ala  Phe  Pro  Glu  Ala  Met  Tyr  Arg
                    325                     330                     335

CGC  ATG  ATA  GAG  ATC  GAG  GTG  CGG  GAG  CCG  GAG  TTG  GAT  CGG  TGG  GCT    1056
Arg  Met  Ile  Glu  Ile  Glu  Val  Arg  Glu  Pro  Glu  Leu  Asp  Arg  Trp  Ala
               340                     345                     350

GAG  ATC  TTC  CCT  GAA  ACG  TGA                                                 1077
Glu  Ile  Phe  Pro  Glu  Thr
               355
```

( 2 ) INFORMATION FOR SEQ ID NO:5:

( i ) SEQUENCE CHARACTERISTICS:
        ( A ) LENGTH: 358 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met  Gly  Ile  Thr  Ile  Lys  Lys  Ser  Thr  Ala  Glu  Gln  Val  Leu  Arg  Lys
1                   5                        10                      15

Ala  Tyr  Glu  Ala  Ala  Ser  Asp  Asp  Val  Phe  Leu  Glu  Asp  Trp  Ile
               20                       25                      30

Phe  Leu  Ala  Thr  Ser  Leu  Arg  Glu  Val  Asp  Ala  Pro  Arg  Thr  Tyr  Thr
               35                       40                      45

Ala  Ala  Leu  Val  Thr  Ala  Leu  Leu  Ala  Arg  Ala  Cys  Asp  Asp  Arg  Val
     50                       55                      60

Asp  Pro  Arg  Ser  Ile  Lys  Glu  Lys  Tyr  Asp  Asp  Arg  Ala  Phe  Ser  Leu
65                       70                      75                      80

Arg  Thr  Leu  Cys  His  Gly  Val  Val  Val  Pro  Met  Ser  Val  Glu  Leu  Gly
                    85                       90                      95

Phe  Asp  Leu  Gly  Ala  Thr  Gly  Arg  Glu  Pro  Ile  Asn  Asn  Gln  Pro  Phe
               100                      105                     110

Phe  Arg  Tyr  Asp  Gln  Tyr  Ser  Glu  Ile  Val  Arg  Val  Gln  Thr  Lys  Ala
               115                      120                     125

Arg  Pro  Tyr  Leu  Asp  Arg  Val  Ser  Ser  Ala  Leu  Ala  Arg  Val  Asp  Glu
     130                      135                     140

Glu  Asp  Tyr  Ser  Thr  Glu  Glu  Ser  Phe  Arg  Ala  Leu  Val  Ala  Val  Leu
145                      150                     155                     160

Ala  Val  Cys  Ile  Ser  Val  Ala  Asn  Lys  Lys  Gln  Arg  Val  Ala  Val  Gly
                    165                      170                     175

Ser  Ala  Ile  Val  Glu  Ala  Ser  Leu  Ile  Ala  Glu  Thr  Gln  Ser  Phe  Val
               180                      185                     190

Val  Ser  Gly  His  Asp  Val  Pro  Arg  Lys  Leu  Gln  Ala  Cys  Val  Ala  Ala
          195                      200                     205

Gly  Leu  Asp  Met  Val  Tyr  Ser  Glu  Val  Val  Ser  Arg  Arg  Ile  Asn  Asp
     210                      215                     220

Pro  Ser  Arg  Asp  Phe  Pro  Gly  Asp  Val  Gln  Val  Ile  Leu  Asp  Gly  Asp
225                      230                     235                     240

Pro  Leu  Leu  Thr  Val  Glu  Val  Arg  Gly  Lys  Ser  Val  Ser  Trp  Glu  Gly
                    245                      250                     255

Leu  Glu  Gln  Phe  Val  Ser  Ser  Ala  Thr  Tyr  Ala  Gly  Phe  Arg  Arg  Val
               260                      265                     270

Ala  Leu  Met  Val  Asp  Ala  Ala  Ser  His  Val  Ser  Leu  Met  Ser  Ala  Asp
               275                      280                     285
```

Asp Leu Thr Ser Ala Leu Glu Arg Lys Tyr Glu Cys Ile Val Lys Val
290                     295                 300

Asn Glu Ser Val Ser Ser Phe Leu Arg Asp Val Phe Val Trp Ser Pro
305                 310                 315                 320

Arg Asp Val His Ser Ile Leu Ser Ala Phe Pro Glu Ala Met Tyr Arg
            325                 330                 335

Arg Met Ile Glu Ile Glu Val Arg Glu Pro Glu Leu Asp Arg Trp Ala
            340                 345                 350

Glu Ile Phe Pro Glu Thr
            355

( 2 ) INFORMATION FOR SEQ ID NO:6:

( i ) SEQUENCE CHARACTERISTICS:
        ( A ) LENGTH: 30 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:6:

Met Gly Ile Thr Ile Lys Lys Ser Glu Ala Glu Gln Val Leu Arg Lys
1               5                   10                  15

Ala Tyr Glu Ala Ala Ser Asp Asp Val Phe Leu Glu Phe
            20                  25                  30

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:7:

Ile Thr Ile Lys Lys
1               5

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:8:

Asp Asp Val Phe Leu Glu Phe
1               5

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:9:

GAGTGAAGCG CGAGGTGCAG CGGCAGA                                                    27

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:10:

AAACGAACTC TCAGGGAAAG TCATGA                                                     26

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:11:

GAAGTGCGTG GAAAGAGCGT GTCG                                                       24

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:12:

GCAATGGATC GCCGTCCAAA ATCA                                                       24

( 2 ) INFORMATION FOR SEQ ID NO:13:

( i ) SEQUENCE CHARACTERISTICS:
        ( A ) LENGTH: 51 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:13:

GATGGGAAGC TTGGAGGTTT AAAAATGGGA ATAACAATTA AAAAGAGCAC G                          51

( 2 ) INFORMATION FOR SEQ ID NO:14:

( i ) SEQUENCE CHARACTERISTICS:
        ( A ) LENGTH: 33 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:14:

TCTGGATCCC GGCGATACAT TGCCTCAGGA AAG                                              33

METHOD FOR CLONING AND PRODUCING THE SACI RESTRICTION ENDONUCLEASE

BACKGROUND OF THE INVENTION

The present invention relates to recombinant DNA which encodes the SacI restriction endonuclease and modification methylase, and the production of SacI restriction endonuclease from the recombinant DNA.

Type II restriction endonucleases are a class of enzymes that occur naturally in bacteria. When they are purified away from other bacterial components, restriction endonucleases can be used in the laboratory to cleave DNA molecules into precise fragments for molecular cloning and gene characterization.

Restriction endonucleases act by recognizing and binding to particular sequences of nucleotides (the 'recognition sequence') along the DNA molecule. Once bound, they cleave the molecule within, or to one side of, the recognition sequence. Different restriction endonucleases have affinity for different recognition sequences. Over one hundred and eighty restriction endonucleases with unique specificities have been identified among the many hundreds of bacterial species that have been examined to date.

Bacteria tend to possess at most, only a small number of restriction endonucleases per species. The endonucleases typically are named according to the bacteria from which they are derived. Thus, the species *Deinococcus radiophilus* for example, synthesizes three different restriction endonucleases, named DraI, DraII and DraIII. These enzymes recognize and cleave the sequences TTTAAA, PuGGNCCPy and CACNNNGTG respectively. *Escherichia coli* RY13, on the other hand, synthesizes only one enzyme, EcoRI, which recognizes the sequence GAATTC.

It is thought that in nature, restriction endonucleases play a protective role in the welfare of the bacterial cell. They enable bacteria to resist infection by foreign DNA molecules like viruses and plasmids that would otherwise destroy or parasitize them. They impart resistance by cleaving invading foreign DNA molecule each time that the recognition sequence occurs. The cleavage that takes place disables many of the infecting genes and renders the DNA susceptible to further degradation by non-specific nucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one or other of the nucleotides within the sequence by the addition of a methyl group. Following methylation, the recognition sequence is no longer cleaved by the restriction endonuclease. The DNA of a bacterial cell is always fully modified by virtue of the activity of its modification methylase. It is therefore completely insensitive to the presence of the endogenous restriction endonuclease. It is only unmodified, and therefore identifiably foreign DNA, that is sensitive to restriction endonuclease recognition and cleavage.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., *Molec. Gen. Genet*, 178:717–719, (1980); HhaII: Mann et al., *Gene*, 3:97–112, (1978); PstI: Walder et al., *Proc. Nat. Acad. Sci.*, 78:1503–1507, (1981)). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acid. Res.*, 12:3659–3676, (1984); PaeR7: Gingeras and Brooks, *Proc. Natl. Acad. Sci.* USA, 80:402–406, (1983); Theriault and Roy, *Gene*, 19:355–359 (1982); PvuII: Blumenthal et al., *J. Bacteriol.*, 164:501–509, (1985)).

A third approach, and one that is being used to clone a growing number of systems are now being cloned by selection for an active methylase gene (refer to EPO Publication No.: 0 193 413 published, Sep. 3, 1986 and BsuRI: Kiss et al., *Nucl. Acid. Res.*, 13:6403–6421, (1985)). Since restriction and modification genes are often closely linked, both genes can often be cloned simultaneously. This selection does not always yield a complete restriction system however, but instead yields only the methylase gene (BspRI: Szomolanyi et al., *Gene*, 10:219–225, (1980); Bcn I: Janulaitis et al, *Gene*, 20:197–204 (1982); Bsu RI: Kiss and Baldauf, *Gene*, 21:111–119, (1983); and Msp I: Walder et al., *J. Biol. Chem.*, 258:1235–1241, (1983)).

A more recent method of cloning (the "endo-blue method") has been described for direct cloning of restriction endonuclease genes in *E. coli* based on the indicator strain of *E. coli* containing the dinD::lacZ fusion (Fomenkov et al., *Nucl. Acids Res.*, 22:2399–2403 (1994)). This method utilizes the *E. coli* SOS response following DNA damage by the endonucleases or non-specific nucleases. A number of thermostable nuclease genes (Tth111I, BsoBI, Thermus nuclease) have been cloned by this method (patent application pending).

Another obstacle to cloning these systems in *E. coli* was discovered in the process of cloning diverse methylases. Many *E. coli* strains (including those normally used in cloning) have systems that resist the introduction of DNA containing cytosine methylation. (Raleigh and Wilson, *Proc. Natl. Acad. Sci.*, USA, 83:9070–9074, (1986)). Therefore, it is also necessary to carefully consider which *E. coli* strain(s) to use for cloning.

Because purified restriction endonucleases, and to a lesser extent, modification methylases, are useful tools for characterizing genes in the laboratory, there is a commercial incentive to obtain bacterial strains through recombinant DNA techniques that synthesize these enzymes in abundance. Such strains would be useful because they would simplify the task of purification as well as providing the means for production in commercially useful amounts.

When foreign restriction modification systems are cloned and introduced into *E. coli*, sometimes the methylase and endonuclease yield is very low compared to the native endonuclease-producing strain probably due to inefficient transcription or translation of the genes in *E. coli*. This is particularly true for cloning of Streptomyces genes into *E. coli* because of the different GC contents of the two microorganisms. It would be desirable to have a cloning system that Streptomyces genes can be sufficiently expressed in *E. coli* and selected for based on the efficient gene expression.

SUMMARY

The present invention relates to a method for cloning the SacI restriction endonuclease gene from Streptomyces into *E. coli* by the methylase selection method. At first, the standard methylase gene selection method was tried to clone the SacI methylase gene using standard cloning vectors such as pBR322 and pUC19 during library construction. The SacI methylase gene was refractory to cloning by using the conventional cloning vectors, presumably due to the poor expression of the SacI methylase gene in *E. coli*. If the SacI methylase is not efficiently expressed in *E. coli*, the SacI sites on the plasmid will not be efficiently modified by the methylase. As a consequence, the plasmid will be cleaved and lost in the plasmid library after SacI endonuclease challenge. Since the standard methylase selection did not work, the "endo-blue method" was used to clone the SacI endonuclease gene. More then twenty blue clones were identified, but none of them yielded any detectable SacI endonuclease activity. A second approach using PCR DNA amplification was used to clone the beginning of the SacI endonuclease gene. Degenerate primers were made based on the SacI protein N-terminal sequence and used to amplify the 87 bp (29 codons) coding sequence. Short PCR products were obtained, cloned into pUC19, and DNA sequences determined. It was found that the PCR products are primer multimers.

In order to increase SacI methylase gene expression in *E. coli*, a high-copy-number plasmid containing a lacUV5 promoter called pRRS (Skoglund et al. *Gene*, 88:1–5, 1990) was used to clone the SacI methylase gene and used for methylase selection. The SacI methylase gene was successfully cloned in pRRS in four steps: (1) ligation of Sau3AI partially digested genomic DNA and BamHI-cleaved and CIP treated pRRS and transformation of the ligated DNA into *E. coli* RR1 competent cells; (2) preparation of mixed plasmid library; (3) SacI digestion of plasmid DNA library and retransformation of the challenged DNA into RR1 cells; (4) Screening SacI resistant plasmid(s) among the survivors. After the SacI methylase gene was cloned, efforts were made to clone DNA fragments next to the methylase gene. Usually methylase gene and endonuclease genes in a particular restriction-modification system are located next to each other. Colony hybridization was used to screen plasmid library for large insert including the SacI methylase gene and the adjacent DNA. The effort failed to identify any large insert. It was realized that in order to clone the SacI endonuclease gene, one has to increase the SacI methylase gene expression in a compatible plasmid. A good ribosome binding with 6 bp spacing was engineered in front of the ATG start codon (GGAGGTAAATAA (SEQ ID NO:1)). The SacI methylase gene with a good ribosome binding site was cloned into the SalI site of the Tet$^R$ gene of pLG339 (a medium-copy-number vector) so that the sacIM gene is driven by the Tet promoter. *E. coli* chromosomal DNA is fully modified by the SacI methylase. After the pre-protected host was made, the SacI endonuclease gene was cloned by two steps of inverse PCR. The first inverse PCR covered the 70% of the SacI endonuclease gene. The second inverse PCR contained the remaining of the gene. The entire SacI endonuclease gene was cloned by amplifying the gene with polymerase chain reaction from genomic DNA and inserted into pRRS vector.

DETAILED DESCRIPTION OF THE INVENTION

Figure 1:
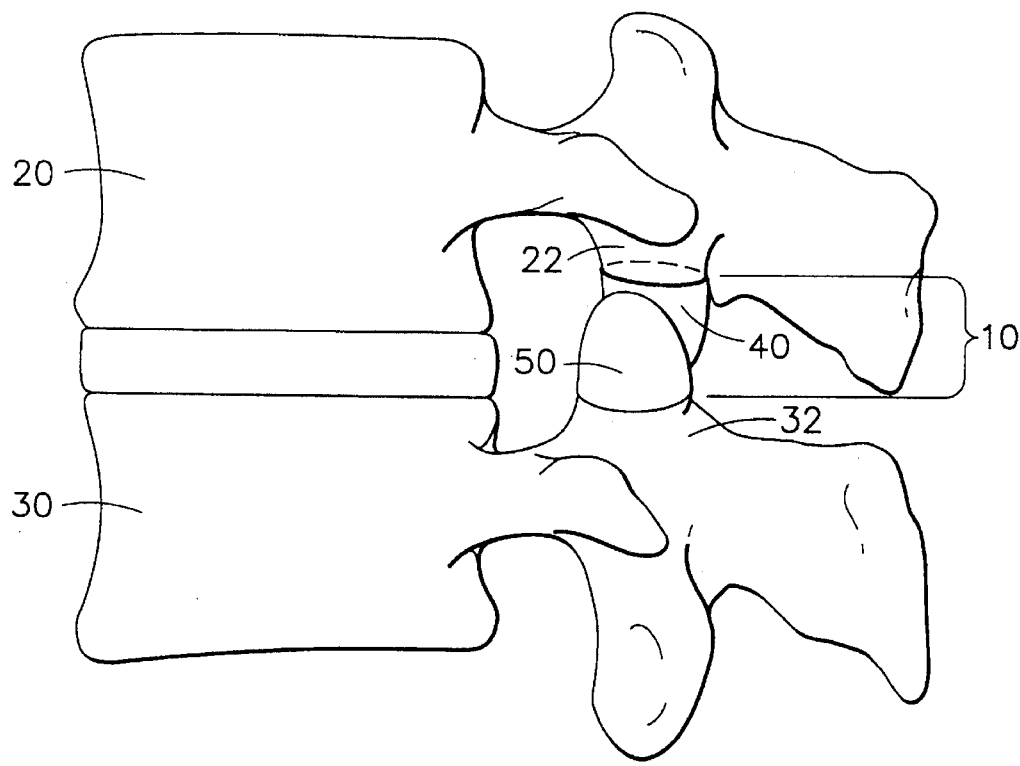
FIG. 1 is a scheme for cloning and producing the SacI restriction endonuclease.

The method described herein by which the SacI methylase gene and endonuclease gene are cloned and expressed is illustrated in FIG. 1 and includes the following steps:

1. The genomic DNA of *Streptomyces achromogenes* is purified.

2. The DNA is digested partially with a restriction endonuclease such as Sau3AI, or any of its isoschizomers, that generates a DNA fragment(s) containing the entire SacI methylase gene. Alternatively, one could make a library which contains the entire restriction-modification system such as ApaLI, SacII, or SalI genomic library. The fragment(s) should also be of clonable size, that is, between 2–20 kb.

3. The Sau3AI-digested genomic DNA is preferably ligated into BamHI-cleaved/CIP treated pUC19 cloning vector. The resulting mixtures are used to transform an appropriate host, i.e. a hsdR$^-$, mcrBC$^-$, mrr$^-$ strain, such as *E. coli* strain RR1. The DNA/cell mixtures are plated on ampicillin selective media for transformed cells. After incubation, the transformed cell colonies are harvested together to form the primary cell library.

4. The recombinant plasmids are purified in toto from the primary cell library to make primary plasmid library. The purified plasmid library is then digested to completion in vitro with SacI endonuclease, or any SacI isoschizomer. SacI endonuclease digestion causes the selective destruction of unmodified, non-methylase-containing clones, resulting in an increase in the relative frequency of SacI methylase-carrying clones.

5. Identification of SacI methylase clone: The digested plasmid library DNA is transformed back into a host such as *E. coli* strain RR1 and transformed colonies are again obtained by plating on ampicillin plates. The colonies are picked and their plasmid DNAs are prepared and analyzed for the presence of the SacI methylase gene by incubating purified plasmid DNA in vitro with SacI endonuclease to determine whether it is resistant to SacI digestion.

6. Once it has been established that the methylase gene has been cloned, the clone is analyzed by restriction mapping and deletion mapping. The entire insert is sequenced to determine the DNA sequence of the SacI methylase gene.

7. Once the methylase gene sequence is determined, two sets of primers are designed which anneal to the beginning and to the end of the methylase gene. Inverse PCR is used to amplify DNA sequence that is adjacent to the methylase gene 8. *Streptomyces achromogenes* genomic DNA is preferably digested with ApaLI, BsrFI, EaeI, EagI, HaeII, NgoMI, PstI, SalI, SacII or TaqI restriction enzymes or any other restriction enzymes that will give rise to reasonable size template DNA (less than 3 kb) for inverse PCR reaction. The digested DNA are self-ligated at a low DNA concentration (less than 2 microgram per ml). The ligated circular DNA is used as templates for inverse PCR reaction using a set of primers that annealed to the end of the SacI methylase gene.

9. After obtaining the inverse PCR products, the DNA is treated with T4 DNA kinase and DNA polymerase and cloned into HincII-cleaved/CIP treated pUC19 vector. The entire inserts are sequenced and the DNA sequences are translated into amino acid sequences in all six reading frames and then compared with the amino acid sequences to the SacI N-terminus protein sequence. One open reading frame of 804 bp is identified that has 27 amino acids identity with the SacI protein sequence. No stop codon was found at the end of the 804 bp sequence, indicating the SacI endonuclease gene has not ended yet.

10. *Streptomyces achromogenes* genomic DNA is digested with AatII, ApaI, BsaWI, BssHII, EaeI, HaeII, MseI, NcoI, NlaIII, PvuI or TaqI restriction enzymes or any other restriction enzymes that will give rise to reasonable size template DNA (less than 3 kb) for inverse PCR reaction. The digested DNA are self-ligated at a low DNA concentration (less than 2 mg/ml). The ligated circular DNA is used as templates for inverse PCR reaction using a set of primers that annealed to the end of the 804 bp open reading frame. After getting the inverse PCR products, the DNA is treated with T4 DNA kinase and DNA polymerase and cloned into HincII-cleaved/CIP treated pUC19 vector. The insert is sequenced until a stop codon is found. The entire SacI endonuclease gene was found to be 1077 bp. It was cloned by two steps of inverse PCR.

11. The SacI methylase gene is then cloned into a pSC101 derivative to premodify *E. coli* host. The entire SacI endonuclease gene is amplified by PCR with two primers. The forward primer contains the ribosome binding site and 7 bp spacing before the ATG start codon. The SacI endonuclease gene is then cloned into expression vector pRRS and transformed into SacI methylase premodified cells.

The following example is given to illustrate embodiments of the present invention as it is presently preferred to practice. It will be understood that this example is illustrative, and that the invention is not to be considered as restricted thereto except as indicated in the appended claims

EXAMPLE 1

CLONING OF SacI RESTRICTION-MODIFICATION SYSTEM

1. Using the "endo-blue method" to clone SacI endonuclease gene.

It was reasoned that if the SacI endonuclease gene is poorly expressed in *E. coli* cell, one may use the "endo-blue method" to clone the endonuclease gene directly into *E. coli* without the SacI methylase protection. Sau3AI partially digested SacI genomic DNA was ligated to BamHI-digested/CIP treated pUC19 and transformed into *E. coli* indicator strain carrying din1::lacZ fusion and plated on X-gal indicator plates. Twenty-six blue colonies were found among 10,000 $Ap^R$ transformants. Plasmid DNA were prepared from all these blue isolates and used to hybridize a degenerate probe that was designed from the SacI N-terminus protein sequence. It was found that one plasmid hybridized to the probe. The DNA sequence was determined for the insert in this plasmid. No significant identity was found between the translated amino acid sequences and the SacI protein sequence except a stretch of four amino acid identity. The degenerate probe was designed from amino acid sequence that includes these four amino acid residues. No SacI activity was found in the cell extracts of all the blue isolates.

2. Using PCR to amplify the beginning of the SacI endonuclease gene.

The N-terminus sequence of SacI protein was determined as (M)GI TIKKSE(or T)AEQVLRKAYEAAASDDVFLEF(or D) (SEQ ID NO:6). Degenerate primers were designed from amino acid residues ITIKK (SEQ ID NO:7) and DDVFLEF (SEQ ID NO:8) and used to amplify 84 bp beginning of the SacI endonuclease gene in a PCR reaction (95° C. 1 min, 30° C. 1 min, 40 cycles). The PCR products were treated with T4 DNA kinase and DNA polymerase and cloned into HincII-cleaved/CIP treated pUC19. The insert DNA was sequenced. It was found that all the inserts are concatemers of primers (primer-dimers).

3. SacI methylase selection using pUC19 as a cloning vector.

AatII, BamHI, NarI, Sau3AI and SphI genomic DNA libraries were constructed using pUC19 as a cloning vector as following: AatII, BamHI, NarI, and SphI digested *S. achromogenes* genomic DNA were ligated to AatII, BamHI, NarI, and SphI-cleaved/CIP treated pUC19 vector; Sau3AI partially digested *S. achromogenes* genomic DNA were ligated to BamHI cleaved/CIP treated pUC19 DNA. Ligated DNA were transformed into RR1 competent cells and plated on Ampicillin plates. A total of $1-5\times10^4$ cells were found in each transformation. Plasmid DNAs were prepared from each primary cell library and cleaved with SacI restriction endonuclease. The SacI-digested DNAs were retransformed into RR1 competent cells. Plasmid DNAs were isolated again from the surviving transformants and digested with SacI restriction enzyme to see if the plasmid DNA is resistant to SacI digestion. 108 plasmids were checked for resistance to SacI digestion from each library. Fourteen resistant clones were found that have lost the SacI site in the vector. No true resistant clones were found in all five libraries.

4. SacI methylase selection using pRRS as a cloning vector.

The methylase selection method requires that the SacI methylase gene to be expressed to a reasonable level in vivo so that the methylase can modify the SacI site on the vector that carries the gene. It is known that Streptomyces genes are poorly expressed in *E. coli* due to the different GC contents of the two microorganisms. In order to express the SacI methylase gene to a high level, another high-copy-number vector pRRS was used as a cloning vehicle. Plasmid pRRS carries the lacUV5 promoter which is stronger than the regular lac promoter on pUC19. Genes cloned into the multiple cloning sites are driven by the lacUV5 promoter. Sau3AI partially digested *S. achromogenes* genomic DNA was ligated to the BamHI digested/CIP treated pRRS vector and the ligated DNA transformed into RR1 competent cells. A total of 10000 of $Ap^R$ transformants were obtained as the primary cell library. Plasmid DNA was prepared from the primary cell library, cleaved with SacI restriction enzyme, and transformed back into RR1 competent cells. The surviving transformants were picked and cultured. Plasmid DNA was isolated from these cells. To examine if any one of these plasmids contain SacI methylase gene, the individual plasmid was digested with SacI endonuclease. One plasmid was found to be truly resistant to SacI digestion. This plasmid carries approximately 1500 bp insert. Deletion of a PstI fragment (about 320 bp) or a HincII fragment (about 1200 bp) of the insert inactivate the SacI methylase gene and render the deletion clones sensitive to SacI endonuclease cleavage.

Figure 2:
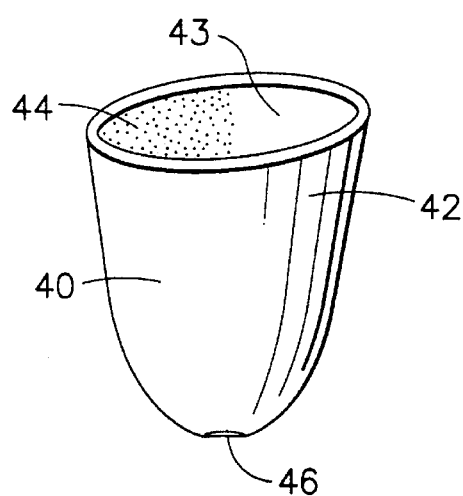
FIG. 2 is the DNA sequence (SEQ ID NO:2 and corresponding amino acid sequence SEQ ID NO:3) of saclM gene and its encoded protein sequence.

The entire SacI methylase gene was sequenced using deletion clones (PstI fragment deletion, HincII fragment deletion, EagI/BamHI fragment deletion, EagI/EcoRI deletion, XbaI/AflII fragment deletion, and Exonuclease III/Mung bean nuclease deletions). The DNA sequence and the predicted amino acid sequence are shown in FIG. 2.

5. Cloning of SacI endonuclease gene

Construction PvuII genomic DNA library: A Southern blot of genomic DNA analysis indicated that a 10 kb PvuII restriction fragment should cover both the SacI methylase gene and the endonuclease gene. PvuII fragments within 8 to 12 kb were gel-purified and ligated into HincII cleaved/CIP treated pUC19 and the ligated DNA transformed into RR1 competent cells. Colony hybridization was performed using SacI methylase gene as a probe. However, no true positive clones were identified.

Cloning of SacI endonuclease gene by inverse PCR: Inverse PCR is an efficient way to clone adjacent DNA to the known DNA sequence. *S. achromogenes* genomic DNA was digested with AatII, AvrII, BamHI, ClaI, EcoRI, EcoRV, HindIII, KpnI, MluI, NcoI, NarI, PstI, PvuII, SmaI, SphI, SalI, XbaI, or XhoI. Each digested DNA was self-ligated to circularize at a low DNA concentration (2 µg/ml in 500 µl total volume). The ligated DNA was extracted once with Phenol-CHCl$_3$, and once with CHCl$_3$ and precipitated with 95% ethanol. The DNA was used as a template for inverse PCR reaction (95° C. 1 min, 60° C. 1 min, 72° C. 5 min, 30 cycles). One set of primers that annealed to the end of the methylase gene was designed as following: forward primer, 5'-GAGTGAAGCGCGAGGTGCAGCGGCAGA-3'(SEQ ID NO:9), reverse primer, 5'-AAACGAACTCTCAGG-GAAAGTCATG A-3'(SEQ ID NO:10). A 900 bp and 4000 bp inverse PCR products were found in the self-ligated PstI genomic DNA and SphI genomic DNA respectively.

To further increase the efficiency of inverse PCR reaction, *S. achromogenes* genomic DNA was digested with more frequent cutting restriction enzymes such as BsrFI, EaeI, HaeII, TaqI and NgoMI restriction enzyme whose recognition sequence is all GC base pairs. It is desirable to use restriction enzymes that will give rise to reasonable size template DNA (less than 3 kb) for efficient inverse PCR reaction. Amplified products were found in BsrFI, EaeI, HaeII, PstI, TaqI and NgoMI digested and self-ligated DNA in the inverse PCR reaction. The NgoMI and HaeII inverse PCR products were treated with T4 DNA kinase, DNA polymerase and cloned into pUC19. The inserts were sequenced and the new sequence was translated in all six frames. The translated amine acid sequences were compared with SacI N-terminus protein sequence. It was found that the SacI endonuclease gene is 22 bp downstream of the SacI methylase gene. One open reading frame of 804 bp is identified that has 27 amine acids identity with the SacI protein sequence. No stop codon was found at the end of the 804 bp sequence, indicating the SacI endonuclease gene has not ended yet. To clone the rest of the SacI endonuclease gene, another set of primers were designed to annealed to the end of the known DNA sequence as follows: forward primer, 5'-GAAGTGCGTGGAAAGAGCGTG TCG-3' (SEQ ID NO:11); reverse primer, 5'-GCAATGGATCGCCG TCCAAAATCA-3' (SEQ ID NO:12). *S. achromogenes* genomic DNA was digested with AatII, ApaI, BsaWI, BssHII, EaeI, HaeII, MseI, NcoI, NlaIII, PvuI or TaqI restriction enzymes. The digested DNAs were self-ligated at a low DNA concentration (less than 2 µg/per ml). The ligated circular DNA was used as templates for inverse PCR reaction (95° C. 1 min, 60° C. 1 min, 72° C. 1 min, 30 cycles). Inverse PCR products were found in the ligated DNA of AatII, BsaW1, BssHII, NlaIII, PvuI, and HaeII digested/self-ligated DNA. The inverse PCR products from HaeII and PvuI were treated with T4 DNA kinase and DNA polymerase and cloned into HincII-cleaved/CIP treated pUC19 vector. The insert was sequenced until a stop codon was found. The entire SacI endonuclease gene was found to be 1077 bp, encoding a protein of 41 kDa.

6. Expression of SacI endonuclease in *E. coli*.

The SacI methylase gene was subcloned into a pSC101 derivative pLG339 to premodify *E. coli* host. The entire SacI endonuclease gene was amplified by PCR with two primers. The forward primer contains the ribosome binding site and 7 bp spacing before the ATG start codon (forward primer, 5'-CATGGGAAGCTTGGAGGTTTAAAAATGG-GAATAA CAATTAAAAAGAGCACG-3' (SEQ ID NO:13); reverse primer, 5'-TCTGG ATCCCGGCG ATA-CATTGCCTCAGGAAAG-3' (SEQ ID NO:14)). The SacI endonuclease gene flanked by HindIII and BamHI sites was cloned into expression vector pRRS and transformed into SacI methylase premodified cells. 500 ml of cells (NEB#963) carrying pRRS-SacIR$^+$ and pLG-SacIM$^+$ was grown to 120 klett units at 30° C. in LB plus Ap (100 µg/ml) and Km (50 µg/ml) and the SacI production was induced for 4 hours by addition of IPTG to 0.5 mM. Cells were harvested and resuspended in 30 ml of sonication buffer. Cell lysis was completed by addition of lysozyme to 100 µg/ml and sonication. Cell debris was removed by centrifugation. The cell extract was diluted 10, 100, 1000, and 10000-fold in TE buffer. 5 µl of the diluted extract was used to digest 1 µg HindIII-cleaved λ DNA for 1 hour at 37° C. The digested DNA was resolved in an 0.8% agarose gel. It was found that the clone makes $1.5 \times 10^6$ units of SacI endonuclease/gram of wet *E. coli* cells. A sample of *E. coli* RR1 containing the SacI restriction modification system (NEB#963) has been deposited under the Budapest Treaty with the American Type Culture Collection on Mar. 22, 1995 and received ATCC Accession No. 69767

What is claimed is:

1. Isolated DNA coding for the SacI restriction endonuclease, wherein the isolated DNA is obtainable from the host *Streptomyces achromogenes*.

2. A recombinant DNA vector comprising a vector into which a DNA segment coding for the SacI restriction endonuclease has been inserted.

3. Isolated DNA coding for the SacI restriction endonuclease and methylase, wherein the isolated DNA is obtainable from ATCC No. 69767.

4. A cloning vector which comprises the isolated DNA of claim 3.

5. A host cell transformed by the cloning vector of claim 2 or 4.

6. A method of producing an SacI restriction endonuclease comprising culturing a host cell transformed with the vector of claim 2 or 4 under conditions suitable for expression of said endonuclease.

* * * * *

UNITED STATES PATENT AND TRADEMARK OFFICE
CERTIFICATE OF CORRECTION

PATENT NO. : 5,532,153            Page 1 of 21

DATED : July 2, 1996

INVENTOR(S) : Xu, et al.

It is certified that error appears in the above-indentified patent and that said Letters Patent is hereby corrected as shown below:

Cover page, Section [57] ABSTRACT
    line 2, replace "SacI" with --*Sac*I--

Cover page, Section [57] ABSTRACT
    line 4, replace "SacI" with --*Sac*I--

Figure 3:
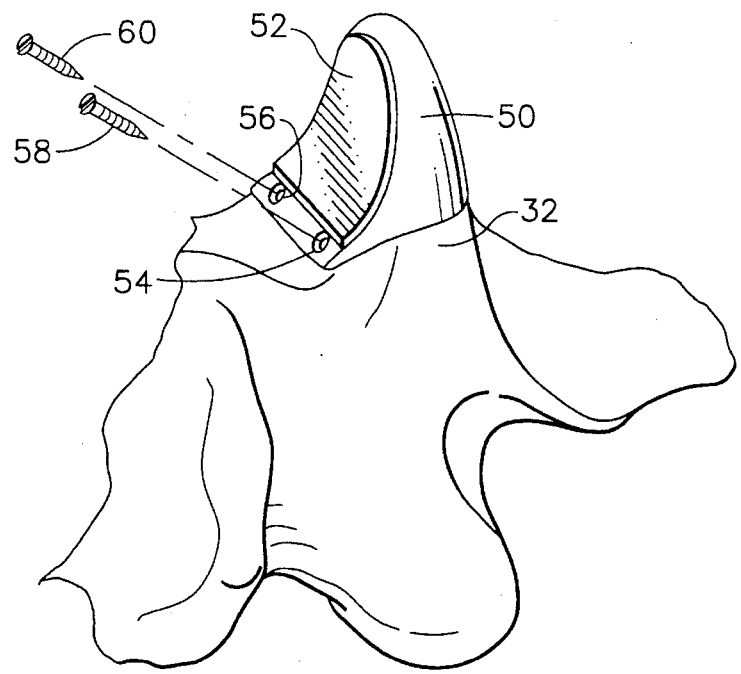
FIG. 3 is the DNA sequence (SEQ ID NO:4 and corresponding amino acid sequence SEQ ID NO:5) of saclR gene and its encoded protein sequence.
Figure 4:
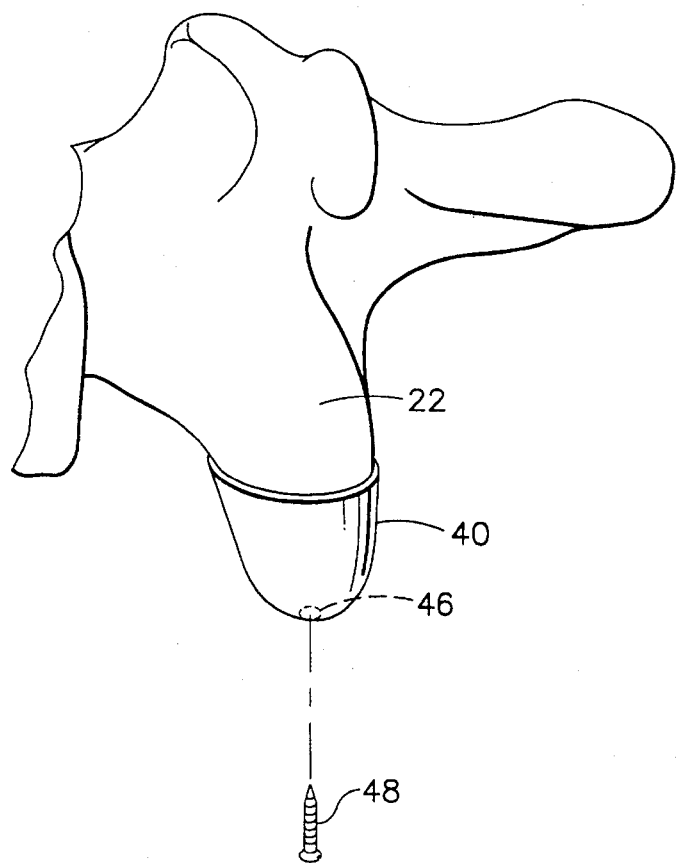
Figure 5:
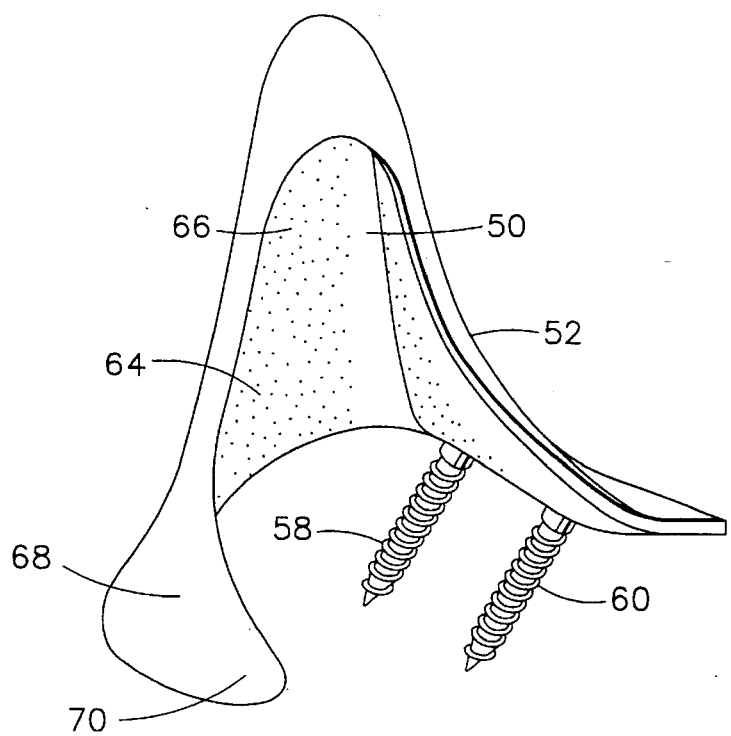
Figure 6:
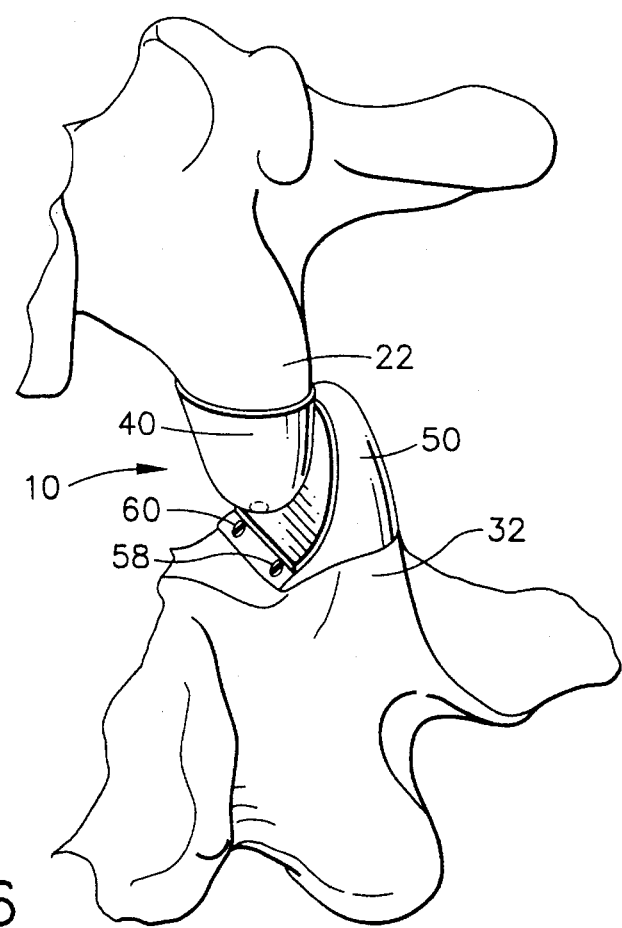
Figure 1:
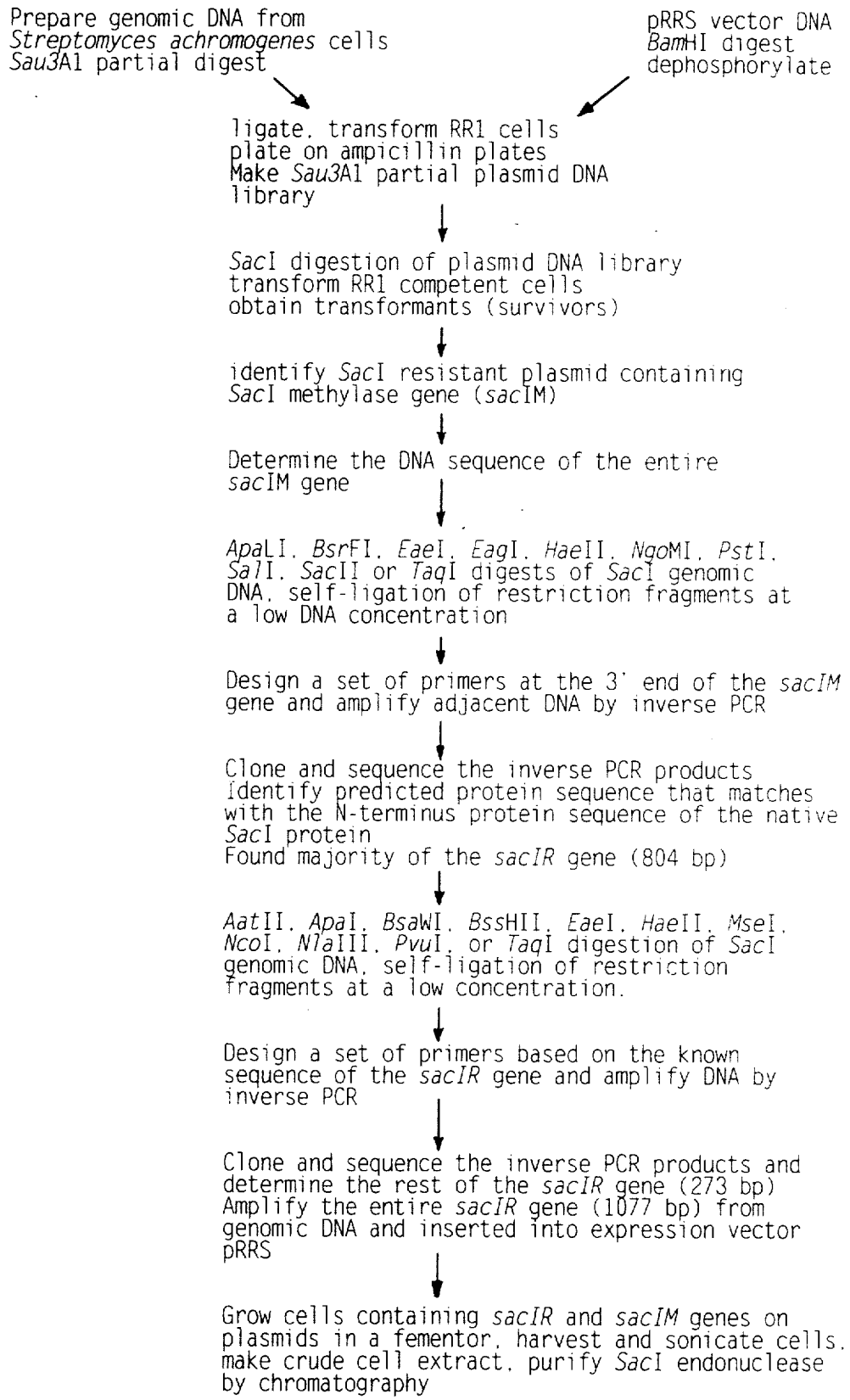

Sheets 1-3, replace Figures 1 through 6 with the attached Figures 1-3

Column 1, line 6, replace "SacI" with --*Sac*I--

Column 1, line 8, replace "SacI" with --*Sac*I--

Column 1, line 30, replace "DraI, DraII and DraIII" with --*Dra*I, *Dra*II and *Dra*III--

Column 1, line 34, replace "EcoRI" with --*Eco*RI--

Column 2, line 3, replace "$10^{-3}$ to $10^{-4}$" with --$10^{-3}$ to $10^{-4}$--

Column 2, line 9, replace "EcoRII" with --*Eco*RII--

Column 2, line 10, replace "HhaII" with --*Hha*II--

Column 2, line 11, replace "PstI" with --*Pst*I--

```
Prepare genomic DNA from                    pRRS vector DNA BamHI
Steptomyces achromogenes cells              digest dephosphorylate
Sau3AI partial digest
                       ↘         ↙
          ligate, transform RR1 cells
          plate on ampicillan plates
          Make Sau3AI partial plasmid DNA
          library
                       ↓
          SacI digestion of plasmid DNA library
          transform RR1 competent cells
          obtain transformants (survivors
                       ↓
          identify SacI resistant plasmid
          containing SacI methylase gene (sacIM)
                       ↓
          Determine the DNA sequence of the entire
          sacIM gene
                       ↓
          ApaLI, BsrFI, EaeI, EagI, HaeII, NgoMI,
          PstI, SalI, SacII or TaqI digests of
          SacI genomic DNA, self-ligation of
          restriction fragments at a low DNA
          concentration
                       ↓
          Design a set of primers of the 3' end of the
          sacIM gene and amplify adjaent DNA by inverse
          PCR
                       ↓
          Clone and sequence the inverse PR products
          Identify predited protein sequence that matches
          with the N-terminus protein sequence of the native
          SacI protien
          Found majority of the sacIR gene (804 bp)
                       ↓
          AatII, ApaI, BasWI, BssHII, EaeI, HaeII, MseI,
          NocI NlaIII, PvuI or TaqI digestion of SacI
          genomic DNA, self-ligation restriction fragments
          at a low concentration
                       ↓
          Design a set of primers based on the known
          sequence of the sacIR gene and amplify DNA
          by inverse PCR
                       ↓
          Clone and sequence the inverse PCR products and
          determine the rest of the sacIR gene (273 bp)
          Amplify the entire sacIR gene (177 bp) from
          genomic DNA and inserted into expression vetor PRRS
                       ↓
          Grow cells containing sacIR and sacIM genes on
          plasmids in a fementor, harvest and sonicate
          cells, make crude cell extract, purify SacI
          endonuclease by chromatography
```

FIG. 1

SacI methylase gene and its gene product

```
GTGAACCATGAGCTTCCTGTGATCAGTCTGTTCTCCGGGGCCGGTGGCCTCGACTGCGCC
 M  N  H  E  L  P  V  I  S  L  F  S  G  A  G  G  L  D  C  A

ATCGAGAGCTGCGCTGAGCCACCGCTGGTCCAGGACGGCTCCGGGTCTCCGCTACGTGTC
 I  E  S  C  A  E  P  P  L  V  Q  D  G  S  G  S  P  L  R  V

GCGGTTGCCACTGACTATGAGCAGACCGCTCTGGATACACTGTCGGCCAACTTCCCGCAC
 A  V  A  T  D  Y  E  Q  T  A  L  D  T  L  S  A  N  F  P  H

ACCAAGACGCTGTGTGGGGATATCCAAACGATCCCGACCGCAGAGTTGCTGGAAGCCGGC
 T  K  T  L  C  G  D  I  Q  T  I  P  T  A  E  L  L  E  A  G

GGGCTGAAGCCCGGCGATCCCACCCTGGTCATCGGTGGTCCTCCTTGTACGCCGTTCAGT
 G  L  K  P  G  D  P  T  L  V  I  G  G  P  P  C  T  P  F  S

AAGTCCGGATTCTGGATCGAGGAGAAGCGCAACAGCGCCGATCCCAATGCCTCCCTCCTT
 K  S  G  F  W  I  E  E  K  R  N  S  A  D  P  N  A  S  L  L

GACGAGTACGTCCGTGTGGTTCGGGAGAGCAAGCCCGAAGCCTTCATCCTGGAAAATGTG
 D  E  Y  V  R  V  V  R  E  S  K  P  E  A  F  I  L  E  N  V

CAGGGCCTGACGTACAAGACCCATCAGGCTCAGTTCGACCGACTCATTGCGGGCCTTAAG
 Q  G  L  T  Y  K  T  H  Q  A  Q  F  D  R  L  I  A  G  L  K

GATGCGGGCTACAACCCGACGTTCCGTGTGCTCCTTGCGGCCGAGTATGGGGTTCCGCAG
 D  A  G  Y  N  P  T  F  R  V  L  L  A  A  E  Y  G  V  P  Q

CTCCGCAGGCGAGTATTCGTTGTGGGGCGACGTGACGGTAAGGCTTTCCACTTCCCCGAA
 L  R  R  R  V  F  V  V  G  R  R  D  G  K  A  F  H  F  P  E

ACCACGCACTCTGGCGAGTCGGAGCGGGATCGGGTGATTGATCACACCAAGATTCCGTTC
 T  T  H  S  G  E  S  E  R  D  R  V  I  D  H  T  K  I  P  F

ACGAGTCTTCGCGAGGCACTTGCCGGACTGCCGGACGTTCCTGAGGCTGGAGAAGTTGTT
 T  S  L  R  E  A  L  A  G  L  P  D  V  P  E  A  G  E  V  V

GAGGGAACCTACGCCGAACTCGCTGCGGAAGTTCCTCCTGGGCAAAACTACCTATGGCAC
 E  G  T  Y  A  E  L  A  A  E  V  P  P  G  Q  N  Y  L  W  H

ACCGACCGATATGGCGGTCGCAACGAGTTCAAATGGCGTAGCCGCTATTGGACCTTCCTG
 T  D  R  Y  G  G  R  N  E  F  K  W  R  S  R  Y  W  T  F  L

CTGAAGGCGGACCCAGACCGCCCTTCTACGACGCTGCAGGCTCAGCCAGGTCCATGGGTC
 L  K  A  D  P  D  R  P  S  T  T  L  Q  A  Q  P  G  P  W  V

GGACCATTTCACTGGGAGAACGTGAAGAACGCGAACGGGGAAGAGCGAGCGCGTAGGTTT
 G  P  F  H  W  E  N  V  K  N  A  N  G  E  E  R  A  R  R  F

CGCGTTGCCGAAATGAAGCGGATCATGACTTTCCCTGATGAGTTCGTTTTCACCGGAGTG
 R  V  A  E  M  K  R  I  M  T  F  P  D  E  F  V  F  T  G  V

AAGCGCGAGGTGCAGCGGCAGATCGGTAATCCCGTCCCGGTGGAGTTGGGGAAGGTCGTC
 K  R  E  V  Q  R  Q  I  G  N  P  V  P  V  E  L  G  K  V  V

GTCCGGGCCCTGATGGAACAACTCGGCTATCTTGATTCTCGCGGTACTACTATTCCTAGC
 V  R  A  L  M  E  Q  L  G  Y  L  D  S  R  G  T  T  I  P  S

CAGGCTGGACACGAACAGCTTGAATTGA
 Q  A  G  H  E  Q  L  E  L
```

FIG. 2

SacI endonuclease gene and its encoded gene product

```
ATGGGAATAACAATTAAAAAGAGCACGGCGGAGCAGGTTTTGAGGAAGGCGTACGAGGCG
 M  G  I  T  I  K  K  S  T  A  E  Q  V  L  R  K  A  Y  E  A
GCCGCTTCGGATGACGTATTCCTCGAAGATTGGATATTTCTGGCTACTTCGCTACGCGAG
 A  A  S  D  D  V  F  L  E  D  W  I  F  L  A  T  S  L  R  E
GTAGATGCTCCAAGGATCTTACACGGCTGCGCTTGTGACAGCACTGCTCGCGCGTGCATGT
 V  D  A  P  R  I  Y  T  A  A  L  V  T  A  L  L  A  R  A  C
GACGACAGGGTTGACCCACGCTCTATCAAAGAGAAGTACGACGATCGCGCCTTCTCTCTG
 D  D  R  V  D  P  R  S  I  K  E  K  Y  D  D  R  A  F  S  L
CGTACCCTTTGCCACGGTGTAGTGGTTCCGATGTCCGTAGAACTTGGATTTGATCTGGGG
 R  T  L  C  H  G  V  V  V  P  M  S  V  E  L  G  F  D  L  G
GCTACGGGCCGCGAGCCGATCAACAATCAGCCATTCTTCCGTTACGACCAATACAGCGAG
 A  T  G  R  E  P  I  N  N  Q  P  F  F  R  Y  D  Q  Y  S  E
ATCGTCAGGGTCCAGATCAAGGCGCGCCCCTATCTGGACCGAGTAAGCAGTGCCCTTGCT
 I  V  R  V  Q  I  K  A  R  P  Y  L  D  R  V  S  S  A  L  A
AGGGTCGATGAAGAAGACTATTCCACTGAAGAGTCGTTCCGAGCGCTTGTCGCTGTCTTG
 R  V  D  E  E  D  Y  S  T  E  E  S  F  R  A  L  V  A  V  L
GCCGTGTGTATCTCTGTGGCGAACAAAAAGCAGCGCGTTGCCGTCGGGAGTGCCATCGTC
 A  V  C  I  S  V  A  N  K  K  Q  R  V  A  V  G  S  A  I  V
GAGGCGAGCCTAATCGCTGAGACTCAGAGCTTCGTTGTGAGTGGCCACGACGTTCCACGA
 E  A  S  L  I  A  E  T  Q  S  F  V  V  S  G  H  D  V  P  R
AAGCTGCAGGCTTGTGTTGCGGCTGGTCTTGACATGGTCTACAGCGAGGTCGTCTCGCGG
 K  L  Q  A  C  V  A  A  G  L  D  M  V  Y  S  E  V  V  S  R
AGGATCAATGACCCTTCTCGCGACTTTCCTGGTGACGTCCAAGTGATTTTGGACGGCGAT
 R  I  N  D  P  S  R  D  F  P  G  D  V  Q  V  I  L  D  G  D
CCATTGCTTACCGTTGAAGTGCGTGGAAAGAGCGTGTCGTGGGAGGGGCTTGAGCAATTC
 P  L  L  T  V  E  V  R  G  K  S  V  S  W  E  G  L  E  Q  F
GTCAGCAGTGCAACGTATGCCGGCTTCCGACGAGTTGCGCTCATGGTCGATGCGGCGTCG
 V  S  S  A  T  Y  A  G  F  R  R  V  A  L  M  V  D  A  A  S
CACGTGTCGCTTATGTCGGCCGATGATCTGACCAGCGCGCTTGAGCGGAAGTACGAGTGC
 H  V  S  L  M  S  A  D  D  L  T  S  A  L  E  R  K  Y  E  C
ATCGTCAAGGTGAACGAGAGCGTGTCGAGCTTCCTGCGTGACGTATTCGTCTGGTCGCCT
 I  V  K  V  N  E  S  V  S  S  F  L  R  D  V  F  V  W  S  P
CGCGACGTCCACTCGATTCTTTCGGCCTTTCCTGAGGCAATGTATCGCCGCATGATAGAG
 R  D  V  H  S  I  L  S  A  F  P  E  A  M  Y  R  R  M  I  E
ATCGAGGTGCGGGAGCCGGAGTTGGATCGGTGGGCTGAGATCTTCCCTGAAACGTGA
 I  E  V  R  E  P  E  L  D  R  W  A  E  I  F  P  E  T  *
```

FIG. 3

UNITED STATES PATENT AND TRADEMARK OFFICE
CERTIFICATE OF CORRECTION

PATENT NO. : 5,532,153

DATED : July 2, 1996

INVENTOR(S) : Xu, et al.

It is certified that error appears in the above-indentified patent and that said Letters Patent is hereby corrected as shown below:

Column 2, line 23, replace "EcoRV" with --*Eco*RV--
Column 2, line 24, replace "PaeR7" with --*Pae*R7--

Column 2, line 26, replace "PvuII" with --*Pvu*II--

Column 2, line 31, replace "BsuRI" with --*Bsu*RI--

Column 2, line 36, replace "BspRI" with --*Bsp*RI--

Column 2, line 37, replace "BcnI" with --*Bcn*I--

Column 2, line 38, replace "Bsu RI" with --*Bsu*RI--

Column 2, line 39, replace "Msp I" with --*Msp*I--

Column 2, line 44, replace "dinD::lacZ" with --*dinD::lacZ*--

Column 2, line 48, replace "Tth111I, BsoBI" with --*Tth*111I, *Bso*BI--

Column 3, line 6, replace "Streptomyces" with --*Streptomyces*--

Column 3, line 9, replace "Streptomyces" with --*Streptomyces*--

Column 3, line 14, replace "SacI" with --*Sac*I--

UNITED STATES PATENT AND TRADEMARK OFFICE
CERTIFICATE OF CORRECTION

PATENT NO. : 5,532,153

DATED : July 2, 1996

INVENTOR(S) : Xu, et al.

It is certified that error appears in the above-indentified patent and that said Letters Patent is hereby corrected as shown below:

Column 3, line 14, replace "Streptomyces" with --*Streptomyces*--

Column 3, line 18, replace "SacI" with --*SacI*--

Column 3, line 19, replace "SacI" with --*SacI*--

Column 3, line 22, replace both "SacI" with --*SacI*--

Column 3, line 23, replace "SacI" with --*SacI*--

Column 3, line 26, replace "SacI" with --*SacI*--

Column 3, line 28, replace "SacI" with --*SacI*--

Column 3, line 30, replace "SacI" with --*SacI*--

Column 3, line 32, replace "SacI" with --*SacI*--

Column 3, line 34, replace "SacI" with --*SacI*--

Column 3, line 39, replace "SacI" with --*SacI*--

Column 3, line 42, replace "SacI" with --*SacI*--

Column 3, line 43, replace "SacI" with --*SacI*--

UNITED STATES PATENT AND TRADEMARK OFFICE
CERTIFICATE OF CORRECTION

PATENT NO. : 5,532,153

DATED : July 2, 1996

INVENTOR(S) : Xu, et al.

It is certified that error appears in the above-indentified patent and that said Letters Patent is hereby corrected as shown below:

Column 3, line 44, replace "Sau3AI" with --*Sau*3AI--

Coumn 3, line 45, replace "BamHI" with --*Bam*HI--

Column 3, line 48, replace "SacI" with --*Sac*I--

Column 3, line 50, replace "SacI" with --*Sac*I--

Column 3, line 51, replace "SacI" with --*Sac*I--

Column 3, line 56, replace "SacI" with --*Sac*I--

Column 3, line 58, replace "SacI" with --*Sac*I--

Column 3, line 59, replace "SacI" with --*Sac*I--

Column 3, line 63, replace "SacI" with --*Sac*I--

Column 3, replace 64, replace "SalI" with --*Sal*I--

Column 3, line 65, relace "sacIM" with --*sacIM*--

Column 3, line 67, replace "SacI" with --*Sac*I--

UNITED STATES PATENT AND TRADEMARK OFFICE
CERTIFICATE OF CORRECTION

PATENT NO. : 5,532,153

DATED : July 2, 1996

INVENTOR(S) : Xu, et al.

It is certified that error appears in the above-indentified patent and that said Letters Patent is hereby corrected as shown below:

Column 4, line 1, replace "SacI" with --*Sac*I--

Column 4, line 3, replace "SacI" with --*Sac*I--

Column 4, line 5, replace "SacI" with --*Sac*I--

Column 4, line 11, replace "SacI" with --*Sac*I--

Column 4, line 14, replace "sacIM" with --*sac*IM--

Column 4, line 17, replace "sacIR" with --*sac*IR--

Column 4, line 23, replace "SacI" with --*Sac*I--

Column 4, line 29, replace "Sau3AI" with --*Sau*3AI--

Column 4, line 30, repalce "SacI" with --*Sac*I--

Column 4, line 33, replace "ApaLI, SacII, or SalI" with --*Apa*LI, *Sac*II, or *Sal*I--

Column 4, line 36, replace "Sau3AI" with --*Sau*3AI--

Column 4, line 37, replace "BamHI" with --*Bam*HI--

UNITED STATES PATENT AND TRADEMARK OFFICE
CERTIFICATE OF CORRECTION

PATENT NO. : 5,532,153  Page 9 of 21
DATED : July 2, 1996
INVENTOR(S) : Xu, et al.

It is certified that error appears in the above-indentified patent and that said Letters Patent is hereby corrected as shown below:

Column 4, line 44, replace "in toto" with --*in toto*--

Column 4, lines 46-47, replace "in vitro with SacI" with --*in vitro* with *Sac*I--

Column 4, line 47, replace both "SacI" with --*Sac*I--

Column 4, line 50, replace "SacI" with --*Sac*I--

Column 4, line 52, replace "SacI" with --*Sac*I--

Column 4, line 57, replace "SacI" with --*Sac*I--

Column 4, line 58, replace "in vitro with SacI" with --*in vitro* with *Sac*I--

Column 4, line 59, replace "SacI" with --*Sac*I--

Column 4, line 63, replace "SacI" with --*Sac*I--

Column 5, lines 4-5, replace "ApaLI, BsrFI, EaeI, EagI, HaeII, NgoMI, PstI, SalI, SacII or TaqI" with --*Apa*LI, *Bsr*FI, *Eae*I, *Eag*I, *Hae*II, *Ngo*MI, *Pst*I, *Sal*I, *Sac*II or *Taq*I--

UNITED STATES PATENT AND TRADEMARK OFFICE
CERTIFICATE OF CORRECTION

PATENT NO. : 5,532,153  Page 10 of 21
DATED : July 2, 1996
INVENTOR(S) : Xu, et al.

It is certified that error appears in the above-indentified patent and that said Letters Patent is hereby corrected as shown below:

Column 5, line 11, replace "SacI" with --*Sac*I--

Column 5, line 15, replace "HincII" with --*Hinc*II--

Column 5, line 20, replace "SacI" with --*Sac*I--

Column 5, line 22, replace "SacI" with --*Sac*I--

Column 5, line 23, replace "SacI" with --*Sac*I--

Column 5, lines 26-27, replace "AatII, ApaI, BsaWI, BssHII, EaeI, HaeII, MseI, NcoI, NlaIII, PvuI or TaqI" with
--*Aat*II, *Apa*I, *Bsa*WI, *Bss*HII, *Eae*I, *Hae*II, *Mse*I, *Nco*I, *Nla*III, *Pvu*I or *Taq*I--

Column 5, line 37, replace "HincII" with --*Hinc*II--

Column 5, line 38, replace "SacI" with --*Sac*I--

Column 5, line 42, replace "SacI" with --*Sac*I--

Column 5, line 14, replace "T4 DNA" with --T4 polynucleotide--

Column 5, line 36, replace "T4 DNA" with --T4 polynucleotide--

Column 5, line 55, replace "claims" with --claims.--

UNITED STATES PATENT AND TRADEMARK OFFICE
CERTIFICATE OF CORRECTION

PATENT NO. : 5,532,153

DATED : July 2, 1996

INVENTOR(S) : Xu, et al.

It is certified that error appears in the above-indentified patent and that said Letters Patent is hereby corrected as shown below:

Column 6, line 3, replace "*din1::lacZ*" with --*dinD1::lacZ*--

Column 6, line 29, replace "T4 DNA" with --T4 polynucleotide--

Column 6, line 45, replace "Ampicillin" with --ampicillin--

Column 7, line 8, replace "10000" with --10,000--

Column 7, line 17, replace "1500" with --1,500--

Column 8, line 5, replace "T4 DNA" with --T4 polynucleotide--

Column 8, line 16, replace "annealed" with --anneal--

Column 8, line 32, replace "T4 DNA" with --T4 polynucleotide--

Column 8, line 58, replace "1000, and 10000-fold" with -1,000 and 10,000-fold--

Column 5, line 43, replace "SacI" with --*SacI*--

Column 5, line 46, replace "SacI" with --*SacI*--

Column 5, line 48, replace "SacI" with --*SacI*--

UNITED STATES PATENT AND TRADEMARK OFFICE
CERTIFICATE OF CORRECTION

PATENT NO. : 5,532,153

DATED : July 2, 1996

INVENTOR(S) : Xu, et al.

It is certified that error appears in the above-indentified patent and that said Letters Patent is hereby corrected as shown below:

Column 5, line 59, replace "SacI" with --*Sac*I--

Column 5, line 61, replace "SacI" with --*Sac*I--

Column 5, line 63, replace "SacI" with --*Sac*I--

Column 5, last line, replace "SacI" with --*Sac*I--

Column 5, last line, replace "Sau3AI" with --*Sau*3AI--

Column 6, line 1, replace "SacI" with --*Sac*I--

Column 6, line 1, replace "BamHI" with --*Bam*HI--

Column 6, line 7, replace "SacI" with --*Sac*I--

Column 6, line 11, replace "SacI" with --*Sac*I--

Column 6, line 16, replace "SacI" with --*Sac*I--

Column 6, line 19, replace "SacI" with --*Sac*I--

Column 6, line 21, replace "SacI" with --*Sac*I--

UNITED STATES PATENT AND TRADEMARK OFFICE
CERTIFICATE OF CORRECTION

PATENT NO. : 5,532,153
DATED : July 2, 1996
INVENTOR(S) : Xu, et al.

Page 13 of 21

It is certified that error appears in the above-indentified patent and that said Letters Patent is hereby corrected as shown below:

Column 6, line 26, replace "SacI" with --*Sac*I--

Column 6, line 30, replace "HincII" with --*Hinc*II--

Column 6, line 33, replace "SacI" with --*Sac*I--

Column 6, line 35, replace "AatII, BamHI, NarI, Sau3AI and SphI" with --*Aat*II, *Bam*HI, *Nar*I, *Sau*3AI and *Sph*I--

Column 6, line 37, replace "AatII, BamHI, NarI, and SphI" with --*Aat*II, *Bam*HI, *Nar*I, and *Sph*I--

Column 6, lines 38-39, replace "AatII, BamHI, NarI, and SphI" with --*Aat*II, *Bam*HI, *Nar*I, and *Sph*I--

Column 6, line 39, replace "Sau3AI" with --*Sau*3AI--

Column 6, line 40, replace "BamHI" with --*Bam*HI--

Column 6, line 47, replace "SacI" with --*Sac*I--

Column 6, line 48, replace "SacI" with --*Sac*I--

Column 6, line 51, replace "SacI" with --*Sac*I--

UNITED STATES PATENT AND TRADEMARK OFFICE
CERTIFICATE OF CORRECTION

PATENT NO. : 5,532,153
DATED : July 2, 1996
INVENTOR(S) : Xu, et al.

It is certified that error appears in the above-indentified patent and that said Letters Patent is hereby corrected as shown below:

Column 6, line 52, replace "SacI" with --*SacI*--

Column 6, line 53, replace "SacI" with --*SacI*--

Column 6, line 54, replace "SacI" with --*SacI*--

UNITED STATES PATENT AND TRADEMARK OFFICE
CERTIFICATE OF CORRECTION

PATENT NO. : 5,532,153
DATED : July 2, 1996
INVENTOR(S) : Xu, et al.

It is certified that error appears in the above-indentified patent and that said Letters Patent is hereby corrected as shown below:

Column 6, line 58, replace "SacI" with --*SacI*--

Column 6, line 60, replace "SacI" with --*SacI*--

Column 6, line 61, replace "in vivo" with --*in vivo*--

Column 6, line 62, replace "SacI" with --*SacI*--

Column 6, line 63, replace "Streptomyces" with --*Streptomyces*--

Column 6, line 65, replace "SacI" with --*SacI*--

Column 7, line 5, replace "Sau3AI" with --*Sau3*AI--

Column 7, line 6, replace "BamHI" with --*Bam*HI--

Column 7, line 10, replace "SacI" with --*SacI*--

Column 7, line 14, replace "SacI" with --*SacI*--

Column 7, line 15, replace "SacI" with --*SacI*--

Column 7, line 16, replace "SacI" with --*SacI*--

UNITED STATES PATENT AND TRADEMARK OFFICE
CERTIFICATE OF CORRECTION

PATENT NO. : 5,532,153

DATED : July 2, 1996

INVENTOR(S) : Xu, et al.

It is certified that error appears in the above-indentified patent and that said Letters Patent is hereby corrected as shown below:

Column 7, line 18, replace "PstI" with --*Pst*I--

Column 7, line 18, replace "HincII" with --*Hinc*II--

Column 7, line 19, replace "SacI" with --*Sac*I--

Column 7, line 20, replace "SacI" with --*Sac*I--

Column 7, line 22, replace "SacI" with --*Sac*I--

Column 7, line 23, replace "PstI" with --*Pst*I--

Column 7, lines 23-26, replace "HincII fragment deletion, EagI/BamHI, EagI/EcoRI deletion, XbaI/AflII" with --*Hinc*II fragment deletion, *Eag*I/*Bam*HI, *Eag*I/*Eco*RI deletion, *Xba*I/*Afl*II--

Column 7, line 30, replace "SacI" with --*Sac*I--

Column 7, line 31, replace "PvuII" with --*Pvu*II--

Column 7, line 32, replace "PvuII" with --*Pvu*II--

Column 7, line 33, replace "SacI" with --*Sac*I--

Column 7, line 34, replace "PvuII" with --*Pvu*II--

UNITED STATES PATENT AND TRADEMARK OFFICE
CERTIFICATE OF CORRECTION

PATENT NO. : 5,532,153

DATED : July 2, 1996

INVENTOR(S) : Xu, et al.

It is certified that error appears in the above-indentified patent and that said Letters Patent is hereby corrected as shown below:

Column 7, line 35, replace "HincII" with --*Hinc*II--

Column 7, line 39, replace "SacI" with --*Sac*I--

Column 7, line 41, replace "SacI" with --*Sac*I--

Column 8, line 10, replace "22" with --17--

Column 7, lines 45-47, replace "AatII, AvrII, BamHI, ClaI, EcoRI, EcoRV, HindIII, KpnI, MluI, NcoI, NarI, PstI, PvuII, SmaI, SphI, SalI, XbaI, or XhoI" with --*Aat*II, *Avr*II, *Bam*HI, *Cla*I, *Eco*RI, *Eco*RV, *Hind*III, *Kpn*I, *Mlu*I, *Nco*I, *Nar*I, *Pst*I, *Pvu*II, *Sma*I, *Sph*I, *Sal*I, *Xba*I, or *Xho*I--

Column 7, line 59, replace "PstI" with --*Pst*I--

Column 7, line 60, replace "SphI" with --*Sph*I--

Column 7, line 64-65, replace "BsrFI, EaeI, HaeII, TaqI and NgoMI" with --*Bsr*FI, *Eae*I, *Hae*II, *Taq*I and *Ngo*MI--

Column 8, lines 2-3, replace "BsrFI, EaeI, HaeII, PstI, TaqI and NgoMI" with --*Bsr*FI, *Eae*I, *Hae*II, *Pst*I, *Taq*I and *Ngo*MI--

UNITED STATES PATENT AND TRADEMARK OFFICE
CERTIFICATE OF CORRECTION

PATENT NO. : 5,532,153

DATED : July 2, 1996

INVENTOR(S) : Xu, et al.

It is certified that error appears in the above-indentified patent and that said Letters Patent is hereby corrected as shown below:

Column 8, line 4, replace "NgoMI and HaeII" with
   --*Ngo*MI and *Hae*II--

Column 8, line 8, replace "amine" with --amino--

Column 8, line 9, replace "SacI" with --*Sac*I--

Column 8, line 10, replace both "SacI" with --*Sac*I--

Column 8, line 12, replace "amine" with --amino--

Column 8, line 12, replace "SacI" with --*Sac*I--

Column 8, line 14, replace "SacI" with --*Sac*I--

Column 8, line 15, replace "SacI" with --*Sac*I--

Column 8, lines 22-23, replace "AatII, ApaI, BsaW1, BssHII, EaeI, HaeII, MseI, NcoI, NlaIII, PvuI or TaqI" with
   --*Aat*II, *Apa*I, *Bsa*W1, *Bss*HII, *Eae*I, *Hae*II, *Mse*I, *Nco*I, *Nla*III, *Pvu*I or *Taq*I--

Column 8, line 30, replace "AatII, BsaW1, BssHII, NlaIII, PvuI, and HaeII" with --*Aat*II, *Bsa*W1, *Bss*HII, *Nla*III, *Pvu*I, and *Hae*II--

UNITED STATES PATENT AND TRADEMARK OFFICE
CERTIFICATE OF CORRECTION

PATENT NO. : 5,532,153

DATED : July 2, 1996

INVENTOR(S) : Xu, et al.

It is certified that error appears in the above-indentified patent and that said Letters Patent is hereby corrected as shown below:

Column 8, line 31, replace "HaeII" with --*Hae*II--

Column 8, line 32, replace 'PvuI" with --*Pvu*I--

Column 8, line 33, replace "HincII" with --*Hinc*II--

Column 8, line 35, replace "SacI" with --*Sac*I--

Column 8, line 37, replace "SacI" with --*Sac*I--

Column 8, line 39, replace "SacI" with --*Sac*I--

Column 8, line 40, replace "SacI" with --*Sac*I--

Column 8, line 47, replace "SacI" with --*Sac*I--

Column 8, line 48, replace "HindIII and BamHI" with --*Hind*III and *Bam*HI--

Column 8, line 50, replace "SacI" with --*Sac*I--

Column 8, line 53, replace "SacI" with --*Sac*I--

Column 8, line 60, replace "HindIII" with --*Hind*III--

UNITED STATES PATENT AND TRADEMARK OFFICE
CERTIFICATE OF CORRECTION

PATENT NO. : 5,532,153
DATED : July 2, 1996
INVENTOR(S) : Xu, et al.

It is certified that error appears in the above-indentified patent and that said Letters Patent is hereby corrected as shown below:

Column 8, line 62, replace "SacI" with --*SacI*--

Column 8, line 62, replace "SacI" with --*SacI*--

Column 21, line 66, replace "SacI" with --*SacI*--

Column 23, line 2, replace "SacI" with --*SacI*--

Column 23, line 4, replace "SacI" with --*SacI*--

Column 24, line 3, replace "SacI" with --*SacI*--

Column 19, (ii) Molecule Type:, replace "DNA (genomic)" with --DNA--

Column 21, (ii) Molecule Type:, replace "DNA (genomic)" with --DNA--

Column 21, (ii) Molecule Type:, replace "DNA (genomic)" with --DNA--

Column 21, (ii) Molecule Type:, replace "DNA (genomic)" with --DNA--

UNITED STATES PATENT AND TRADEMARK OFFICE
CERTIFICATE OF CORRECTION

PATENT NO. : 5,532,153

DATED : July 2, 1996

INVENTOR(S) : Xu, et al.

It is certified that error appears in the above-indentified patent and that said Letters Patent is hereby corrected as shown below:

Column 21 (ii) Molecule Type:, replace "DNA (genomic)" with --DNA--

Column 21, (ii) Molecule Type:, replace "DNA (genomic)" with --DNA--

Signed and Sealed this

First Day of April, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.   : 5,532,153
DATED        : July 2, 1996
INVENTOR(S)  : Xu, et al

It is certified that error appears in the above-indentified patent and that said Letters Patent is hereby corrected as shown below:

The Drawing Sheet, consisting of Figure 1, should be deleted and replace with the drawing sheet, consisting of Figure 1, as shown on the attached page.

Signed and Sealed this

Sixteenth Day of September, 1997

Attest:

BRUCE LEHMAN

Attesting Officer

*Commissioner of Patents and Trademarks*